(12) United States Patent
Hauger et al.

(10) Patent No.: US 11,533,465 B2
(45) Date of Patent: Dec. 20, 2022

(54) VISUALIZATION SYSTEM FOR VISUALIZING OF A THREE-DIMENSIONAL TARGET REGION OF AN OBJECT

(71) Applicant: Carl Zeiss Meditec AG, Jena (DE)

(72) Inventors: Christoph Hauger, Aalen (DE); Alois Regensburger, Poxdorf (DE)

(73) Assignee: Carl Zeiss Meditec AG, Jena (DE)

( * ) Notice: Subject to any disclaimer, the term of this patent is extended or adjusted under 35 U.S.C. 154(b) by 1260 days.

(21) Appl. No.: 15/976,775

(22) Filed: May 10, 2018

(65) Prior Publication Data

US 2018/0332270 A1    Nov. 15, 2018

(30) Foreign Application Priority Data

May 10, 2017    (DE) .......................... 102017110103.9

(51) Int. Cl.
*H04N 13/204*    (2018.01)
*A61B 3/00*    (2006.01)
(Continued)

(52) U.S. Cl.
CPC ......... *H04N 13/204* (2018.05); *A61B 3/0025* (2013.01); *A61B 3/102* (2013.01); *A61B 3/13* (2013.01); *A61B 3/14* (2013.01); *A61B 34/20* (2016.02); *A61B 90/20* (2016.02); *A61B 90/361* (2016.02); *A61F 9/007* (2013.01); *G02B 21/0012* (2013.01); *G06T 7/0012* (2013.01);
(Continued)

(58) Field of Classification Search
None
See application file for complete search history.

(56) References Cited

U.S. PATENT DOCUMENTS 9,844,321 B1 * 12/2017 Ekvall ................... A61B 90/37
2008/0077158 A1    3/2008 Haider et al.
(Continued)

FOREIGN PATENT DOCUMENTS

| DE | 10 2013 223 152 A1 | 5/2015 |
| DE | 11 2013 006 234 T5 | 10/2015 |
| WO | WO 2015/071272 A1 | 5/2015 |

OTHER PUBLICATIONS

"Intraoperative optical coherence tomography using the RESCAN 700: preliminary results from the DISCOVER study", Justis P. Ehlers et al., Br J Ophthalmol 2014, vol. 98, pp. 1329-1332 (6 pgs total).
(Continued)

*Primary Examiner* — Chikaodili E Anyikire
(74) *Attorney, Agent, or Firm* — DeWitt LLP

(57) ABSTRACT

A system for visualizing a three-dimensional target area of an object with a measuring device which determines a distance of a surgical instrument in a target area with respect to a predetermined structure in the target area, a display unit for representing the views, and a control unit. The control unit controls the display unit such that the display unit is in a first display mode when a determined distance is greater than a predetermined first limit value, and switches from the first display mode into a second display mode when the determined distance changes from being greater than a predetermined second limit value, which is smaller than or equal to the predetermined first limit value, to smaller than the predetermined second limit value.

9 Claims, 1 Drawing Sheet

(51) Int. Cl.
| | |
|---|---|
| H04N 13/239 | (2018.01) |
| H04N 13/271 | (2018.01) |
| G02B 21/00 | (2006.01) |
| A61B 34/20 | (2016.01) |
| A61B 90/20 | (2016.01) |
| A61B 90/00 | (2016.01) |
| G06T 7/50 | (2017.01) |
| G06T 7/73 | (2017.01) |
| A61B 3/10 | (2006.01) |
| A61B 3/13 | (2006.01) |
| A61B 3/14 | (2006.01) |
| A61F 9/007 | (2006.01) |
| G06T 7/00 | (2017.01) |

(52) U.S. Cl.
CPC ............ *G06T 7/50* (2017.01); *G06T 7/73* (2017.01); *H04N 13/239* (2018.05); *H04N 13/271* (2018.05); *A61B 2034/2055* (2016.02); *A61B 2090/364* (2016.02); *A61B 2090/3735* (2016.02); *G06T 2207/10012* (2013.01); *G06T 2207/10056* (2013.01); *G06T 2207/10101* (2013.01); *G06T 2207/30041* (2013.01)

(56) References Cited

U.S. PATENT DOCUMENTS

| | | | |
|---|---|---|---|
| 2015/0268844 A1* | 9/2015 | Kim | G06F 3/04886 715/822 |
| 2015/0335234 A1 | 11/2015 | Okada et al. | |
| 2016/0183779 A1* | 6/2016 | Ren | A61B 90/20 351/246 |
| 2016/0296375 A1 | 10/2016 | Reich et al. | |
| 2017/0251920 A1* | 9/2017 | Tokuda | A61B 3/113 |
| 2018/0360308 A1* | 12/2018 | Aimi | A61B 3/0025 |

OTHER PUBLICATIONS

"Novel microscope-integrated stereoscopic heads-up display for intrasurgical optical coherence tomography", Liangbo Shen et al, Biomedical Optics Express, pp. 1711-1726, 2016 (16 pgs total).

* cited by examiner

VISUALIZATION SYSTEM FOR VISUALIZING OF A THREE-DIMENSIONAL TARGET REGION OF AN OBJECT

CROSS-REFERENCE TO RELATED APPLICATION

The present application claims the priority of German patent application No. 102017110103.9, filed May 10, 2017, the entirety of which is hereby incorporated by reference herein, including the English translation thereof.

TECHNICAL FIELD

The present invention relates to a visualization system for visualizing a three-dimensional target area of an object and can for example be formed as a stereo surgical microscope.

BACKGROUND

Surgical operating microscopes are used for example in eye surgery for interventions on the anterior and/or posterior chamber of the eye. By means of the stereo surgical microscope, during a surgery the user or surgeon receives a stereoscopic top view of the target area in which the surgery is to be carried out, such that the surgeon can orientate himself well. In the case of such a surgery it is desirable for the surgeon to have a good visual grasp of the distance of the surgical instrument, which he is using, to a predetermined structure in the target area.

The object of the invention is therefore to provide a visualization system for visualizing a three-dimensional target area of an object, with which a good visualization of a distance of a surgical instrument in the target area to a predetermined structure in the target area can be realized.

SUMMARY

The visualization system according to the invention for visualizing a three-dimensional target area of an object can comprise a measuring device which determines a distance of a surgical instrument in the target area to a predetermined structure in the target area, and which generates a first view of the target area as well as a second view with the surgical instrument and the predetermined structure, wherein the second view runs transverse to the first view or wherein the second view does not lie parallel to the first view. Furthermore, the visualization system can comprise a display unit for representing the views and a control unit, wherein the control unit controls the display unit such that it is in a first display mode when the determined distance is greater than a predetermined first limit value, and such that it switches from the first display mode into a second display mode when the determined distance changes from being greater than a predetermined second limit value, which is smaller than or equal to the predetermined first limit value, to being smaller than the predetermined second limit value. In the first display mode of the views, at least the first view is represented and in the second display mode, when the second view is not represented in the first display mode, the second view is represented in the second display mode, or, when the second view is represented in the first display mode, the second view is represented optically highlighted in comparison with the first display mode.

With the visualization system according to the invention, an automatic switching from the first display mode into the second display mode thus takes place when the value falls below the predetermined second limit value. Thus, the first view, which is for example a top view of the target area, can be represented in the first display mode and the second view can then be represented in the second display mode, such that the user or surgeon can visually perceive the distance between his surgical instrument and the predetermined structure well. The second view can be a side view or a sectional view. With the visualization system according to the invention, the surgeon can thus be provided with a good overview of the target area based on the first view in the first display mode, such that the surgeon can orientate himself well. As soon as the surgeon with his surgical instrument is close to the predetermined structure, the system is switched into the second display mode, in which the distance between the surgical instrument and the predetermined structure is visually represented to the surgeon. The first view can of course still additionally be represented in the second display mode. However, it is also possible that the first view is not represented in the second display mode.

By the optically highlighted representation of the second view in the second display mode is meant in particular that the second view is represented larger and/or brighter than in the first display mode and/or at a different position (e.g. more central) on the display unit than in the first display mode. Furthermore, the colour can additionally or alternatively be changed during the representation.

The display unit can represent the first view stereoscopically. Furthermore, the display unit can represent the second view stereoscopically. The first view can in particular be a top view onto the target area. The second view can be a side view or sectional view. The first and second views can be representations of the target area which are perpendicular to each other or form an angle which lies in the range of from 45° to 90°.

The control unit can control the display unit such that it switches from the second display mode into the first display mode when the determined distance changes from being smaller than the predetermined first limit value to being greater than the predetermined first limit value. When the predetermined first limit value is greater than the predetermined second limit value, there is thus a hysteresis which prevents a switching back and forth in the case of small changes in the region of the predetermined first limit value or of the predetermined second limit value.

Furthermore, the control unit can control the display unit such that, before another switching from the first display mode into the second display mode, a predetermined period must have elapsed after the switching from the second display mode into the first display mode. A hysteresis is also generated thereby, which prevents a switching back and forth.

The measuring device can comprise a microscope which generates the first view by means of optical imaging. The microscope can be formed as a stereo microscope and/or as a surgical microscope The measuring device can comprise an optical coherence tomography (OCT) device which generates OCT measurement data covering the entire target area. The OCT measurement data can in particular be used for generating the second view. However, they can also additionally or alternatively be used for generating the first view.

Furthermore, the measuring device can comprise a microscope, the measurement data of which are used for generating the first view and/or the second view. In particular, the measurement data of the microscope and the measurement data of the OCT device can be used together for generating the first view and/or the second view.

Furthermore, the measuring device can comprise a distance measurement unit which (preferably continuously) measures the distance between the surgical instrument and the predetermined structure in the target area.

The display unit can for example be formed as an eyepiece of the microscope. The second view can for example be reflected into the eyepiece. Furthermore, the display unit can be formed as a monitor or screen or as a display device that can be mounted on the head of a user (head-mounted display device=HMD device). The monitor or screen, as well as the HMD device can present the views as two-dimensional views or as three-dimensional views. For example, the first view can be represented three-dimensionally and the second view two- or three-dimensionally.

The OCT device can be based on all known OCT technologies. The OCT device can be a time-domain OCT system, a frequency-domain OCT system, a spectral-domain OCT system and/or a swept-source OCT system.

The OCT device and the microscope can, at least in part, use identical optical elements.

Furthermore, a visualization method for visualizing a three-dimensional target area of an object is provided for a visualization system which comprises a measuring device which determines a distance of a surgical instrument in the target area to a predetermined structure in the target area, and which generates a first view of the target area as well as a second view with the surgical instrument and the predetermined structure, wherein the second view lies transverse to the first view or does not extend parallel to the first view, and a display unit for representing the views. The display unit is controlled such that it is in a first display mode when the determined distance is greater than a predetermined first limit value, and such that it switches from the first display mode into a second display mode when the determined distance changes from being greater than a predetermined second limit value, which is smaller than or equal to the predetermined first limit value, to being smaller than the predetermined second limit value, wherein, in the first display mode of both views, at least the first view is represented and in the second display mode, when the second view is not represented in the first display mode, the second view is represented, or, when the second view is represented in the first display mode, the second view is represented optically highlighted in comparison with the first display mode.

The visualization method according to the invention can comprise the method steps described in connection with the visualization system according to the invention. In the same way, the visualization system according to the invention can comprise elements or components in order to carry out the steps described in connection with the visualization method according to the invention.

Furthermore, a computer program product is provided which comprises software code in order to carry out the steps of the visualization method according to the invention when the product is executed (in particular on a control device or a control unit of a visualization system with the measuring device and the display unit).

It is understood that the features named above and those yet to be explained below can be used not only in the combinations indicated but also in other combinations or alone, without departing from the scope of the present invention.

The above summary is not intended to describe each illustrated embodiment or every implementation of the subject matter hereof. The figures and the detailed description that follow more particularly exemplify various embodiments.

BRIEF DESCRIPTION OF THE DRAWINGS

In the following, the invention is explained in yet more detail by means of embodiment examples with reference to the attached drawings. These embodiment examples merely serve for illustration and are not to be interpreted as limiting. For example, a description of an embodiment example with a plurality of elements or components is not to be interpreted to the effect that all of these elements or components are necessary for the implementation. Rather, other embodiment examples can also contain alternative elements and components, fewer elements or components or additional elements or components. Elements or components of different embodiment examples can be combined with each other, unless otherwise indicated. Modifications and adjustments which are described for one of the embodiment examples can also be applicable to other embodiment examples. For the avoidance of repetition, identical elements or those corresponding to each other are labelled with the same reference numbers in different figures and are not explained multiple times. The figures show.

Figure 1:
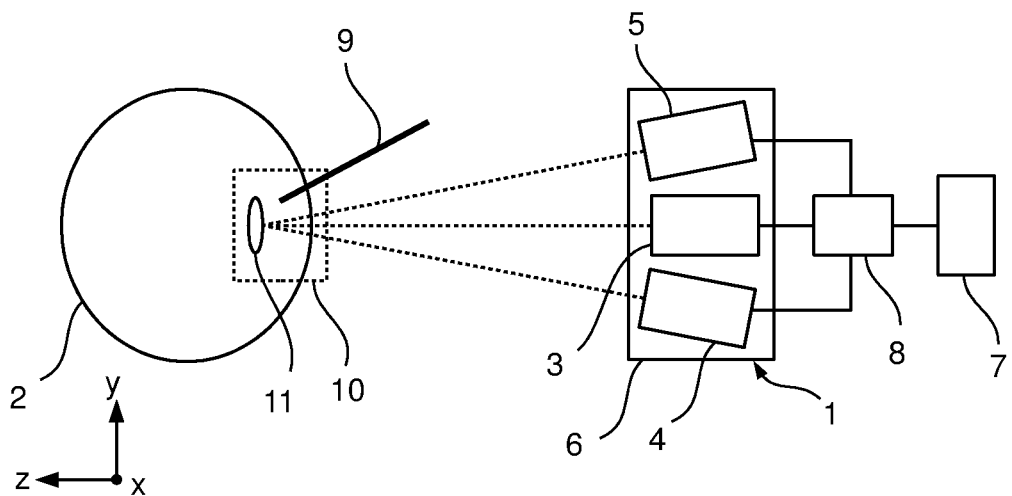
FIG. 1 a schematic representation of a first embodiment example of the visualization system according to the invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

FIG. 1 shows an embodiment example of the visualization system 1 according to the invention for visualizing a three-dimensional target area of an object 2 (here e.g. a human eye). The visualization system 1 comprises a microscope 3 (e.g. a surgical microscope 3), an optical coherence tomography (OCT) device 4 and a distance measurement unit 5. The microscope 3, the OCT device 4 and the distance measurement unit 5 together form a measuring device 6 of the visualization system 1.

Furthermore, the visualization system 1 comprises a display unit 7, as well as a control unit 8. The display unit 7 can e.g. be a binocular eyepiece of the microscope 3, a monitor or a display device that can be mounted on the head (which can also be referred to as an HMD device: head-mounted display device). The display unit 7 can provide a two-dimensional image representation or preferably a three-dimensional image representation or a stereoscopic image representation.

The visualization system 1 can be used e.g. in the field of eye surgery (e.g. for interventions on the anterior and/or posterior chamber of the eye). Frequent interventions on the anterior chamber are e.g. cataract and glaucoma treatments. Membrane peeling and macular hole interventions are frequently carried out on the retina. The embodiment example described here is based on a cataract treatment, wherein a surgical instrument 9, which can be e.g. an aspirator, forceps, bipolar forceps etc., is drawn in schematically.

As the measuring device 6 comprises the microscope 3 and the OCT device 4, the measuring device 6 can provide microscope image data and OCT image data. In the case of the microscope image data, the object 2 is observed from the front in a top view (i.e. virtually in the x-y plane). The microscope 3 is preferably formed as a stereo microscope, such that there is a stereoscopic top view. In the case of the OCT image data, volume data about the entire three-dimensional target area 10, in which the lens 11 to be replaced also lies, can be generated. Based on the OCT image data, present in digital form, the generation of a top view (in the x-y plane), a side view or a sectional image (in each case e.g. in the x-z plane) is possible. A top view of the target area 10 offers the advantage of an overview image, while a side view or a sectional view can better visualize the depth information and the distance of the surgical instrument 9 to the lens 10 and e.g. can enable progress monitoring during the operation.

Figure 2:
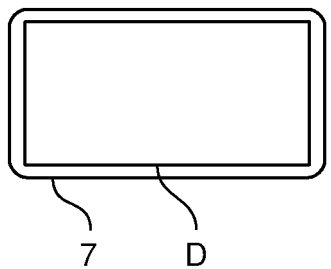
FIG. 2 a schematic representation to explain the representation on the display unit 7 in the first display mode.
Figure 3:
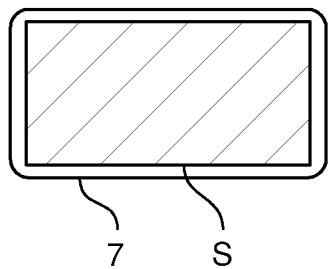
FIG. 3 a schematic representation to explain the representation on the display unit 7 in a second display mode.

The visualization system 1 according to the invention is formed such that an automatic switching between a represented top view (first view) and a represented side view or represented sectional view (second view) is carried out. For this purpose, the control unit 8 continuously assesses the distance between the surgical instrument 9 and the lens 11, measured by means of the distance measurement unit 5. So long as the measured distance is greater than a predetermined switching value, the control unit 8 controls the display unit 7 such that the top view D (first view) of the target area 10 is represented, as is shown schematically in FIG. 2. This can be e.g. the stereoscopic top view D of the microscope 3. The display unit 7 is in a first display mode. If, during the operation, the distance between the surgical instrument 9 and the lens 11 falls below the predetermined switching value, the control unit 8 switches the display unit 7 from its first display mode into a second display mode in which the top view D is no longer represented on the display unit 7, but instead only a side view S or only a sectional view S based on the image data of the OCT device 4 (FIG. 3). The user or operator can thereby see very well visually, how far away he still is with his surgical instrument 9, from the lens 11. Virtually a y-z view is displayed to the user. As the switching from the first display mode into the second display mode based on the measured distance is carried out automatically, an excellent visualization is available to the user, which contributes to very good operation results.

If, in the course of the surgery, the distance between the surgical instrument 9 and the lens 11 changes such that it again becomes greater than the predetermined switching value, the control unit 8 controls the display unit 7 such that it is again switched into the first display mode, in which only the overview image D (or top view D) is represented.

The control unit 8 is preferably formed such that there is a certain hysteresis during the switching in order to avoid a constant switching back and forth between the first and second display mode in the case of very small distance changes. For this purpose, e.g. the distance value for switching from the second display mode into the first display mode can be selected such that it does not correspond to the predetermined switching value, but to a predetermined first limit value which is greater than the predetermined switching value, which can also be referred to as the predetermined second limit value. Thus e.g. a switching from the top view (first display mode) to the side view (second display mode) can be carried out on reaching a distance of e.g. 200 μm (second limit value) based on greater distance values. A switching back into the first display mode and thus a switching from the side view to the top view can only be carried out on reaching a distance of e.g. 350 μm (first limit value). Furthermore, additionally or alternatively, after a switching from the second display mode into the first display mode, another switching into the second display mode can only be carried out when a predetermined minimum period has elapsed. This can be a period of e.g. 1, 2, 3, 4 or 5 seconds. Only after the predetermined minimum period has passed is a switching into the second display mode carried out, when the measured distance between the surgical instrument 9 and the lens 11 reaches or falls below the second limit value.

Typical values for the first and second limit value or the switching value (in particular in eye surgery) can lie in the range of from e.g. 100 μm to 500 μm.

The microscope 3 can be constructed as an analogue microscope or as a digital microscope. In the case of an analogue structure, there is an optical eyepiece and thus analogue image data for the top view are present. The optical eyepiece can be formed such that the image data for the second display mode are reflected in. The reflection can be carried out such that only the image data reflected in are visible. Alternatively, it is possible for the image data reflected in to be additionally visible.

In the case of a digital structure of the operating microscope, digital image data which can be represented in a suitable way are present.

The top view D in the first display mode can be based on the image data of the microscope 3 and/or the OCT image data. When both image data of the microscope 3 and of the OCT device 4 are used, these can be superimposed and/or blended.

In the same way, the image data for the side view or sectional view in the second display mode can be based on the image data of the microscope 3 and/or the image data of the OCT device 4. When image data of the microscope 3 and of the OCT device 4 are used, these can be superimposed and/or blended. The image data of the microscope 3 can be calculated for the side view and represented on the basis of a topography.

The side view can be e.g. a perspective volume representation, a three-dimensional representation or a two-dimensional representation.

Figure 4:
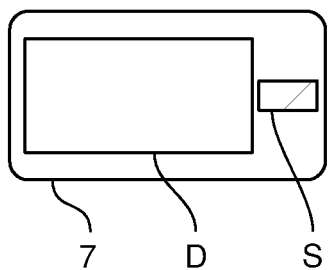
FIG. 4 a schematic representation to explain the representation on the display unit 7 in the first display mode.
Figure 5:
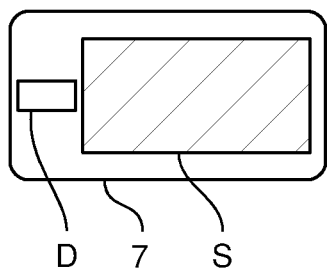
FIG. 5 a schematic representation to explain the representation on the display unit 7 in the second display mode.

In a further embodiment example, the top view D and the side view S (or sectional view S) are represented both in the first display mode and in the second display mode of the display unit 7. However, in the second display mode, the side view S (or sectional view S) is represented optically highlighted in comparison with the side view in the first display mode. This can be effected e.g. in that the size of the representation of the side view S (or sectional view S) in the second display mode (FIG. 5) is greater than in the first display mode (FIG. 4). Of course a representation is also possible, in which there is at least a partial overlapping of side view S (or sectional view S) and top view.

The distance measurement unit can be designed video-, laser- and/or OCT-based. Furthermore, it is possible to realize the distance measurement unit 5 via an intraoperative navigation system or tracking system, as is used e.g. in neurosurgical applications.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A system for visualizing a three-dimensional target area of an object, the system comprising:
    a measuring device which determines a distance of a surgical instrument in the target area to a predetermined structure in the target area, and which generates a first view of the target area as well as a second view including the surgical instrument and the predetermined structure, transverse to the first view;
    a display unit for representing the views; and
    a computer control unit in operable communication with the display unit and which controls the display unit such that it is in a first display mode when the determined distance is greater than a predetermined first limit value, and such that it switches from the first display mode into a second display mode when the determined distance changes from being greater than a predetermined second limit value, which is smaller than or equal to the predetermined first limit value, to being smaller than the predetermined second limit value, wherein, in the first display mode of both views, at least the first view is represented and in the second display mode, when the second view is not represented in the first display mode, the second view is represented or, when the second view is represented in the first display mode, the second view is represented optically highlighted in comparison with the first display mode.

2. The system according to claim 1, in which the first view is a top view onto the target area.

3. The system according to claim 1, in which the display unit represents the first view stereoscopically.

4. The system according to claim 1, in which the control unit controls the display unit such that it switches from the second display mode into the first display mode when the determined distance changes from being smaller than the predetermined first limit value to being greater than the predetermined first limit value.

5. The system according to claim 4, in which the control unit controls the display unit such that, before another switching from the first display mode into the second display mode, a predetermined period must have elapsed after the switching from the second display mode into the first display mode.

6. The system according to claim 1, in which the measuring device comprises a microscope which generates the first view by means of optical imaging.

7. The system according to one of the above claims, in which the measuring device comprises an optical coherence tomography (OCT) device which generates OCT measurement data covering the entire target area.

8. A method for visualizing a three-dimensional target area of an object for a visualization system which comprises a measuring device which determines a distance of a surgical instrument in the target area to a predetermined structure in the target area, and which generates a first view of the target area as well as a second view with the surgical instrument and the predetermined structure transverse to the first view, and a display unit for representing the views, wherein the display unit is controlled such that it is in a first display mode when the determined distance is greater than a predetermined first limit value, and such that it switches from the first display mode into a second display mode when the determined distance changes from being greater than a predetermined second limit value, which is smaller than or equal to the predetermined first limit value, to being smaller than the predetermined second limit value, wherein, in the first display mode of both views, at least the first view is represented and in the second display mode, when the second view is not represented in the first display mode, the second view is represented or, when the second view is represented in the first display mode, the second view is represented optically highlighted in comparison with the first display mode.

9. A non-transitory computer program product which comprises software code in order to carry out the steps of claim 8 when the program is executed.

\* \* \* \* \*